United States Patent
Kitajima (10) Patent No.: US 8,263,842 B2
(45) Date of Patent: Sep. 11, 2012

(54) MADAGASCAR PERIWINKLE WITH FRINGE TYPE FLOWER AND METHOD OF BREEDING THE SAME

(76) Inventor: Osamu Kitajima, Sakurai (JP)

( * ) Notice: Subject to any disclaimer, the term of this patent is extended or adjusted under 35 U.S.C. 154(b) by 1026 days.

(21) Appl. No.: 11/578,506

(22) PCT Filed: Apr. 15, 2005

(86) PCT No.: PCT/JP2005/007332
§ 371 (c)(1),
(2), (4) Date: Aug. 6, 2007

(87) PCT Pub. No.: WO2005/099442
PCT Pub. Date: Oct. 27, 2005

(65) Prior Publication Data
US 2007/0283454 A1    Dec. 6, 2007

(30) Foreign Application Priority Data

Apr. 16, 2004  (JP) .................................. 2004-121210

(51) Int. Cl.
*A01H 5/00*    (2006.01)
(52) U.S. Cl. ....................................... 800/323; 800/298
(58) Field of Classification Search .................. 800/298, 800/323
See application file for complete search history.

(56) References Cited

U.S. PATENT DOCUMENTS

| | | | | |
|---|---|---|---|---|
| 5,491,285 A | * | 2/1996 | Bowman | ........................ 800/265 |
| 5,633,441 A | * | 5/1997 | De Greef et al. | ............. 800/271 |
| 6,166,306 A | | 12/2000 | Bowman | |
| PP17,766 P2 | * | 5/2007 | Kitajima | |
| 2002/0069433 A1 | | 6/2002 | Schmidt et al. | |
| 2003/0110539 A1 | | 6/2003 | Sase | |

FOREIGN PATENT DOCUMENTS

JP     10-127196 A     5/1998
WO     WO 97/43427 A1  11/1997

OTHER PUBLICATIONS

Mishra et al. Manifestation of heterostyle character by induction of recessive hsf mutation responsible for thrum type herkogamous flowers in *Catharanthus roseus*. Journal of Medicinal and Aromatic Plant Scienceds 25 (2003) pp. 2-7.*
The New Royal Horticultural Society Dictionary of Gardening, vol. 1, 1992, p. 541.*
International Search Report of the International Searching Authority mailed on Jun. 21, 2005 for the corresponding international patent application No. PCT/JP2005/007332 (English version enclosed).

* cited by examiner

*Primary Examiner* — June Hwu
(74) *Attorney, Agent, or Firm* — Posz Law Group, PLC (57) ABSTRACT

A fringe flowered Madagascar periwinkle, especially a long blooming Madagascar periwinkle having a pistil without pollination ability. A fringe flowered Madagascar periwinkle bred by pollinating a pollen of a fringe flowered Madagascar periwinkle to a commercial variety, and a fringe flowered Madagascar periwinkle obtained by self pollinating a fringe flowered and pistil sterile Madagascan periwinkle.

11 Claims, 10 Drawing Sheets

(a) acute    (b) mucronate    (c) obtuse

Fig. 10

MADAGASCAR PERIWINKLE WITH FRINGE TYPE FLOWER AND METHOD OF BREEDING THE SAME

TECHNICAL FIELD

The present invention relates to the breeding method of fringe blooming Madagascar periwinkle.

BACKGROUND ART

Madagascar periwinkle (the previous scientific name: vinca) is native to Madagascar, Rep. of, Java, India and Brazil, and is fruticose herbaceous perennial. taxonomically, it belongs to *Apocynaseae Catharanthus*, and the scientific name is *Catharanthus roseus* L. (the previous scientific name: *Vinca rosea* L.). Recently the improved varieties which are dwarf, large and have many flowers is marketed. The flower color is red-purple, peach and white and so on, and the center is ordinarily deep.

The flower whose hem is notched or rippling is called fringe blooming flower, and it is known with tulip, pansy (viola) and so on. The fringe blooming flower gives the gorgeous impression and is admitted it has high market value. However, about flowers of Madagascar periwinkle, Madagascar periwinkle whose flower edge is roud has been known, but fringe flowered one have not been known. Therefore, the breeding Madagascar periwinkle which has fringe blooming flower have been demanded.

The blooming period of Madagascar periwinkle is ordinarily short, within a several days to about 10 days, out doors, and old flower falls naturally. This is because flower withers by pollination by flower's weltering by wind or by insect's taking a flower as usual Madagascar periwinkle has fertility.

There was the problem that the flower doesn't keep for long time in the windy room or outdoors.

To solve these problems, in other flowers, the pollination ability of pollen or pistil is lost by the introduction of sterile trait using crossbreeding (patent literature 1) and by the mutation breeding of heavy ion beam to breed the flowers of long blooming period. However, as the individuals which lack of the pollination ability of pollen or pistil has not existed in Madagascar periwinkle especially fringe flowered Madagascar periwinkle, the breeding of Madagascar periwinkle to keep flowers long, especially fringe flowered Madagascar periwinkle, has been desired.

Moreover it has been desired to develop the breeding method of varieties with variation in flower color or in shape of Madagascar periwinkle which has fringe blooming flowers and long blooming period.

[patent literature 1] JP2004-000103A bulletin, 3 page

DISCLOSURE OF THE INVENTION

The Problem to be Solved

The present invention provides the fringe flowered Madagascar periwinkle. It also provides the Madagascar periwinkle whose pistil does not have the pollination ability and which blooms for long time. Moreover it provides the method to produce Madagascar periwinkle plant which has fringe blooming flower and long blooming period.

Means for Solving the Problem

The inventor is devoted to research to solve the above problem so that he has developed the fringe flowered Madagascar periwinkle and the breeding method of it. The present invention provides inventions as following viewpoint.

From the first standpoint, Madagascar periwinkle comprising fringe blooming flowers is provided. According to the present invention, the effect to enhance ornamental value of flowers by fringed flowers can be obtained. In this specification 'fringe flowered' or 'fringe blooming' means the petal patterns that the hem of petals is notched, that the hem of petals has lacinia, or that the hem of petals becomes the projection of filamentous or string condition. The notched shapes may be sharp or smooth, and may be straight, curved, filamentous or string. If it is the fringe blooming, it may be screwed, or united with the form of other flowers and such as rose blooming. Either flower color is not limited. The degree of the lacinia of the fringe is 0.1~50% of the radius of petals, more preferable about 1~30%, more preferable about 1~20%, the most preferable about 2~15%.

Next, from the second standpoint, Madagascar periwinkle whose pistil does not have fertility is provided. The flower whose pistil does not have fertility has the effect that blooming period is longer outdoors than that of the flower whose pistil has fertility.

From the third standpoint, Madagascar periwinkle comprising fringe blooming flowers and pistil which does not have fertility is provided. According to the present invention, the effect can be obtained to get the high ornament-valued and long-flower-keeping Madagascar periwinkle plant. In the present specification, the 'long-flower-keeping' means that the blooming period becomes longer without pollination by weltering in the wind or by insect mediation. It does not mean that blooming period is longer than that of the ordinary Madagascar periwinkle in the environment of no wind and no insect.

From the forth standpoint, Madagascar periwinkle comprising fringe blooming flower and pollen which has fertility is provided. Using the pollen of Madagascar periwinkle of the present invention, the effect can be obtained to hand down the fringe flowered character to progeny by crossing.

From the fifth standpoint, Madagascar periwinkle comprising fringe blooming flowers, Pistil which does not have fertility and pollen which has fertility is provided. According to the present invention, the effect can be obtained to get Madagascar periwinkle plant which has high ornament-value and flowers of long blooming period and which can be used as pollen parent. In the present specification, 'long blooming period' means that blooming period lengthens by eliminating pollination by wind or by insects, and does not mean that blooming period lengthens in the environment without wind and insect.

From the sixth standpoint, Madagascar periwinkle comprising fringe blooming flowers, pistil which does not have fertility, pollen which has fertility, and marcescent flower which does not fall even if it withers is provided. This brings about the effect to have the ornamental-valued and long blooming flowers, to use as a pollen-parent and to reduce the work to clean up floor in the indoor cultivation.

From the seventh standpoint, a cell, an organ, a tissue, a plant body, a seed or a pollen cell of Madagascar periwinkle according to one of $1^{st}$ standpoint to $6^{th}$ standpoint is provided. According to the present invention, as a part of the plant is provided, the effect can be obtained to use them for cell-culture, organ-culture and tissue-culture and enables to store seed, to sell seed, to crossbreeding using pollen, and to cultivate pollen cell.

From the eighth standpoint, a plant, a cell, a tissue, a plant body, a seed or a pollen cell and their progenies produced by crossing with Madagascar periwinkle according to one of $1^{st}$ standpoint to $6^{th}$ standpoint are provided. According to the present invention, the effect can be obtained that effective utilization of progeny by crossbreeding becomes possible.

From the ninth standpoint, method for producing Madagascar periwinkle comprising fringe blooming flower by cross breeding or by mutation breeding, using Madagascar periwinkle according to one of $1^{st}$ standpoint to $6^{th}$ standpoint is provided. According to the present invention, the effect can be obtained to get various variations of Madagascar periwinkle plant which has fringe blooming flowers.

From the tenth standpoint, a method for producing Madagascar periwinkle comprising flower which does not have fertility by crossbreeding or by mutation breeding, using Madagascar periwinkle according to one of $1^{st}$ standpoint to $6^{th}$ standpoint is provided. According to the present invention, the effect can be obtained to get Madagascar periwinkle plant which has fringe blooming flowers and long blooming period because of sterility.

From the eleventh standpoint, progeny plant or its part obtained by using Madagascar periwinkle according to one of $1^{st}$ standpoint to $6^{th}$ standpoint is obtained. According to the present invention, the progeny plant or the part of Madagascar periwinkle which has fringe blooming and/or sterile flowers can be obtained. In this specification, a part of plant body means, for example, organ such as leaf, stem, flower, root, seed and so on, and cuttings, cultured tissue, cultured cell, pollen and so on, a part is possible even if it is not a complete plant body.

From the twelfth standpoint, part of Madagascar periwinkle plant according to one of $1^{st}$ standpoint to $6^{th}$ standpoint is provided. According to the present invention provides cut flowers, cutting spike, seeds etc. which has fringe blooming flowers and/or long blooming period flowers.

From the thirteenth standpoint, method for producing fringe flowered Madagascar periwinkle by pollinating a pollen of Madagascar periwinkle comprising fringe flowered trait and a pollen which has fertility to a pistil of other Madagascar periwinkles is provided. According to the present invention, the effect can be obtained making possible to produce Madagascar periwinkle plant by crossbreeding which has fringe blooming flowers.

From the fourteenth standpoint, method for selecting Madagascar periwinkle which has weekly fringed flower at F1 generation by pollinating a pollen of Madagascar periwinkle comprising fringe blooming trait and a pollen which has fertility to a pistil of other ordinary Madagascar periwinkles which have ordinary petals. According to the present invention, Madagascar periwinkle which has weekly fringe blooming flower by pollinating pollen of the fringed flower to pistil of Madagascar periwinkles which has non-fringed flower. In this case, an ordinary petal means a non-fringed petal.

From the fifteenth standpoint, method for selecting fringed and sterile Madagascar periwinkle plant from flowered individual which is seeded, cultivated from the F2 seed which was obtained by pollinating pollen of the same F1 generation or by pollinating pollen of individual which is fringed and nonfertile to pistil of F1 plant which has weekly fringed flower obtained by standpoint 14 is provided. According to the present invention, Madagascar periwinkles which has strong fringe flowered trait and nonfertile flower can be obtained by pollinating self-pollinated pollen or by cross-pollination of F1 generation which has weekly fringed flower obtained by pollen of fringe blooming flower.

The Effect of the Invention

According to the present invention, fringe blooming Madagascar periwinkle and Madagascar periwinkle which has fringe blooming and long blooming flower out of doors are provided

DESCRIPTION OF THE PREFERRED EMBODIMENTS

Deposit Information

A deposit for the microorganism F2 seeds (i.e., Madagascar periwinkle seeds comprising fringe bloom flowers, pistil without fertility and pollen with fertility, as discussed below) was made in accordance with the provisions of the Budapest Treaty on the International Recognition of the Deposit of Microorganisms for the Purposes of Patent Procedure (the Budapest Treaty). The deposit number is FERM BP-11483. The date of the deposit was Mar. 26, 2012, and the deposit was made at the following depositary:

International Patent Organism Depositary
National Institute of Technology and Evaluation
Tsukuba Central 6, 1-1, Higashi 1-chome, Tsukuba-shi, Ibaraki-ken 305-8566, Japan Execution form of this invention is explained below, but this invention is not limited to these.

Inventor has obtained Madagascar periwinkle line (angel chuchu) comprising a fringe blooming flower, a sterile pistil and a fertile pollen in the process of repeating crossbreeding and selection. In the present specification, 'female sterile' means that pistils does not have fertility and are sterile. This Madagascar periwinkle which is fringe flowered, female sterile and whose pollen having fertility, has high appreciation value and moreover it has the characteristics of long flower keeping, because the flowers don't fall by self-pollination for the sake of female sterile.

This Madagascar periwinkle can be propagated vegetatively by cuttings.

The pollen of this Madagascar periwinkle (Angel chuchu) has fertility, and it is possible to pollinate the pistil of wild Madagascar periwinkle, commercial varieties, breeding mother plant ones and the their closely-related plant which can be crossed. By these crossing, weak fringed Madagascar periwinkle can be obtained in F1 generation. In this case, it is possible also to breed varieties which have fringe blooming flowers and different flower colors by crossing varieties having different flower colors. It is also possible to breed varieties which have fringe blooming flowers and different plant shapes by crossing varieties whose shapes are different.

There is a chance to get a plant of good character, and in the case which is possible to be multiplicated by means of vegetative propagation to sell them. Moreover almost all F1 generation has fringed character according to combination of parent plants, and in that case, it is possible to sell F1 seeds.

And in F1 generation, as not only stamen but also pistil has fertility, it is possible to get F2 seeds by self-pollination of F1. It is possible to breed and select variety which has useful character such as color changing variety and the like from F2 generation plant obtained by sowing and growing the F2 seeds.

And by crossing variety which has useful character of dwarfism, large flower and disease resistance and so on, it is possible to breed a variety having fringed flower or being sterile which has these useful characters.

As in this F1 generation the pistil has fertility, it is possible to get F2 seed by self-pollinating F1 individual. Sowing these F2 seeds, getting plants of F2 generation, it is possible to select fringe flowered and female sterile plant from these F2 individuals. As this fringe flowered and female sterile plant is sterile, stylar scar does not occur by self-pollination and blooming period is long. As pollen has fertility, it is possible to use for crossbreeding furthermore.

The female sterile individual obtained by crossing can be multiplied by vegetative propagation; in this case, it is possible to make it virus-free by meristem culture to prevent damage of viral disease. Meristem culture can be performed by the method as is well known to those skilled in the art. That is, stems including the terminal bud or lateral bud of Madagascar periwinkle plant are sterilized in aqueous solution of hypochlorous acid (available chlorine concentration 1%) for 5~15 minutes, after that, washing for four times by sterilized water, clearing hypochlorous acid thoroughly. The shoot apex of this stem is cut out by stereomicroscope, put on hormone free Murashige and Skoog (MS) medium (sucrose 3%, ph5.6 gellan gum 0.25% it may contain 0.05 to 0.1 ppm auxin and cytokinin depending on the variety), culture for three days to one week in the dark condition and after this, cultured in the light condition. When the shoots extend sufficiently, they are put on MS medium which does not contain hormone (concentration of one-half~1 times, sucrose 3%, pH5.6, gellan gum 0.25%), and radicate it. As gel agar can be available, but using gellan gum makes the following operations easier. In this case, MS medium containing 0.05~1 ppm isobultyrate (sucrose 3%, pH5.6, gellan gum 0.25%) can be used. When it takes root sufficiently, washes out agar or gellan gum thoroughly, transplants to vermiculite or florialite, makes it naturalized in the mist room or naturalized by gradually increasing the opening rate of the means to keep the humidity (for example, culture vessel, vinyl cover, and the like) and by dropping humidity. The naturalized plant can be transplanted to the ordinary cultivation soil and the plant body can be obtained. By this means, virus free seedlings can be obtained. It is preferred that the virus free seedlings are maintained as the sterile seedlings, in addition to keep cultivating at the greenhouse of double door to quadplex door with net.

Fringed and female sterile Madagascar periwinkle is different from ordinary one, is not necessary to collect petals of withered flower falling on the floor even if it grows indoors and is easy to grow because s withered flower does not fall. And there is an advantage to be able to grow in the sunshiny room, such as near the window.

Fringe flowered and female sterile Madagascar periwinkle can be propagated by cuttings, breed Madagascar periwinkle which has new flower color and shape by mutation treatment of the propagated Madagascar periwinkle by this means. Hereby, keeping the fringed and female sterile character, by getting various variation plants and propagating them by cuttings, the mutant plant which has useful character can be obtained. This mutation treatment includes the treatment by chemicals, for example, chemicals which has mutagenicity such as nitrosoguanidine, ethylmethane sulfonate and so on, the treatment by radical rays such as gamma ray and the treatment by heavy ion beam etc., but is not limited to these. In the case of using nitrosoguanidine or ethylmethane sulfonate, plant which has good trait can be selected by applying diluted solutions of adequate concentration to plant bud part directly or by inserting cuttings for rooting and culturing them after dipping the part containing shoots in the solution containing mutagen chemicals for several minutes to several tens of minutes and after incorporated the mutagen chemicals at the time of preparing cuttings. Concentration of mutagen in the solution containing mutagen and treatment time can be determined by preliminary test so that the survival rate of the treated material is, for example, about 1~5%.

in the case of gamma ray irradiation, distance is taken from some levels to a dozen levels from radiation source in the radiation breeding field, appropriate number of individuals are planted, irradiated with gamma ray for about a half hour everyday and are introduced mutations. Continuing to cultivate it under this condition, Madagascar periwinkle including various mutations are obtained. It is possible to select good character among them and its trait is fixed by repeating to cross, or it is vegetatively propagated and is sold as it is. Alternatively it is possible to obtain mutant lines by irradiating cultured tissues (adventitious buds etc.), seeds, sections (stem including shoot) by gamma ray irradiation as is well known to those skilled in the art.

In the case of heavy ion beam treatment, seed or section etc. is arranged in a single layer on the petri dish etc. and is irradiated with a heavy ion beam by heavy ion beam generator which is in facility of Institute of RIKEN. In this case, the main experiment is performed after determining the conditions which survival rate is, for example, about 1%~5% by the preliminary experiment. Elite individuals are selected by sowing irradiated seeds or by planting and growing stems containing shoots. Treating target may be tissue culture such as adventitious buds etc., in this case. It is naturalize through regeneration and rooting. Elite individuals obtained by selection may be fixed by repeating crossing or can be propagated by cuttings and sold as it is.

For mutation treatment, tissue culture can be used derived from fringed and female sterile individual. A part of fringed and female sterile individuals are treated by the method as is well known to those skilled in the art, for example, treated by hypochlorous acid for about 5~15 minutes, after being washed four times with plenty quantity of sterilized water, is put on MS medium etc and proliferated. By treating this with the agent with mutagenicity such as nitrosoguanidine, nitrosourea, ethylmethane sulfonate (EMS) and the like for the appropriate time, for example on the condition where the 90~99% of the cells are dead, mutated cells are obtained and plant body can be obtained by regenerating them. Or it is possible to obtain somaclonal variation by going through the tissue culture as is well known to those skilled in the art. The mutant plant obtained by these methods may be fixed by crossing, or may be propagated by means of vegetative reproduction and may be sold.

First Embodiment

Hereinafter, the present invention is explained by examples, but is not limited to the following examples.

When about five thousands of pink variety seeds of commercial Madagascar periwinkle were sowed and growed by the usual method in grass house neighboring inventor's home in 201 Higaida Sakurai, Nara, repeating crossbreeding about various combinations for about 5 generations including seedlings without name which inventor has, one line of pale pink fringe flowered Madagascar periwinkle was obtained. Based on this line, by repeating crossbreeding and selection, fringed and sterile Madagascar periwinkle whose pistil was degenerate was obtained. This line was named angel chuchu. (As to this plant, allotting is guaranteed if inventor is contacted. Application for variety registration about this angel chuchu is filed. The application number of variety registration is 16874.) This plant had characters which was not only fringe flowered but also female sterile, which bloomed for long time and whose marcescent flowers did not fall even if flower withered. When flower was in buds, or immediately after coming into flower, a flower which remained green segments in a part of petals was observed. These green segments disappeared on blooming completely and a whole flower became pink. Then the plant was propagated by cuttings and used for following experiment. The method of herbaceous cutting was performed by the methods which is well known to those skilled in the art. That is, the putting side of cutting including apical bud or gnarl with two or four leaves were lightly adhered to rooting compound, for example isobutyric acid etc., making a herbaceous cutting on vermiculite, keeping the vermiculite without drying until rooting. It may be taken root in the mist room. It may be naturalized in ordinary cultivation soil after rooting and grown as is well known to those skilled in the art.

(Crossing Experiment)

Figure 1:
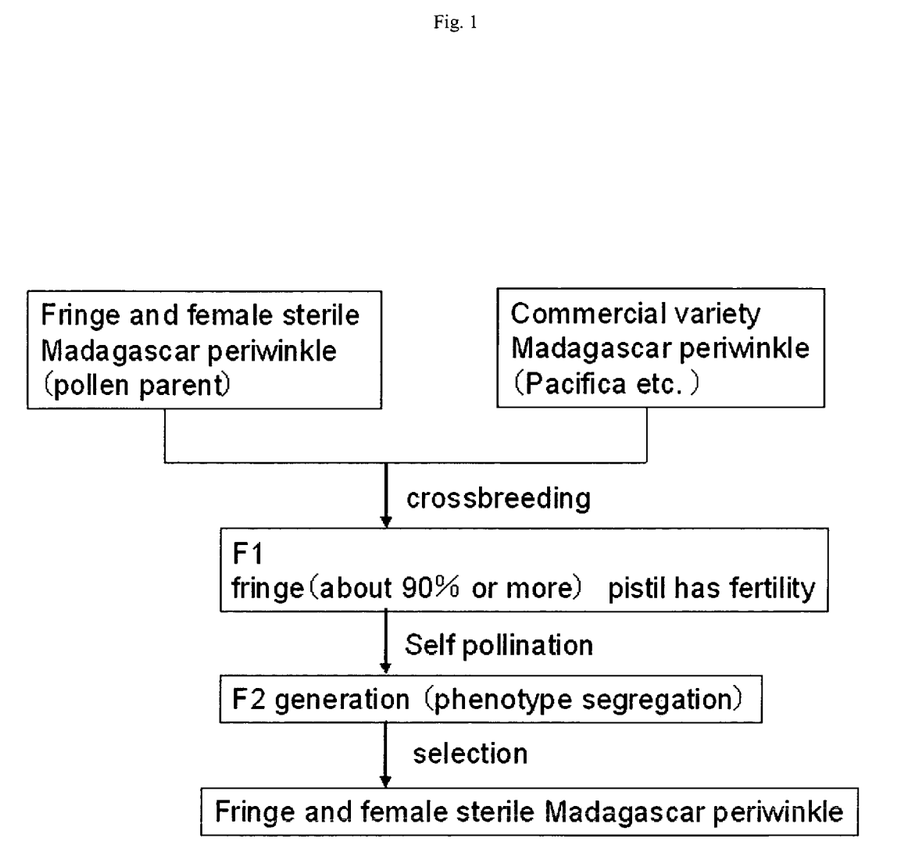
FIG. 1 crossbreeding of fringe flowered Madagascar periwinkle

FIG. 1 shows the flow of crossbreeding of fringe flowered Madagascar periwinkle. 13 varieties, commercial varieties, were grown by method as is well known to those skilled in the art, buds were opened up by scissors at the time of several hours before blossoming, adhered pollen of stamen's anther of the fringe flowered and female sterile Madagascar periwinkle to inner pistil. It was grown until it seeds and seeds were obtained. These seeds (F1 seeds) were sowed and grown; all 13 varieties made weakly fringed flowers blossomed. Though the probability of fringe flowering was fluctuant by varieties, among all the experimented varieties, more than 90% of F1 individuals showed fringe flowered character. (show table 1 below mentioned) Female sterile character was not recognized in F1 individuals. About the flower color there were some patterns, some had pattern near parents, some became flower color different from parents, some segregate to same flower color and different one from parents. Hence it was able to breed Madagascar periwinkle variety which had weakly fringed character in F1 generation and whose flower color is different by pollinating pollens of fringe blooming and female sterile flower to a commercial variety etc. Both pollen and pistil in this F1 generation had fertility.

TABLE 1

| Parent variety pollinated | A number of individuals F1 is near parent variety | A number of individuals F1 is fringed | Fringed ratio (%) |
|---|---|---|---|
| Peppermint | 7 | 484 | 98.6 |
| Pacifica blush | 0 | 363 | 100.0 |
| New magic | 10 | 98 | 90.7 |
| Stardust orchid | 2 | 26 | 92.9 |
| Pacifica coral | 1 | 149 | 99.3 |
| Pacifica cherry red | 14 | 169 | 92.3 |
| Pacifica red | 22 | 222 | 91.0 |
| Pacifica pink | 4 | 337 | 98.8 |
| Apricot | 2 | 309 | 99.4 |
| Pacifica white | 0 | 242 | 100.0 |
| pale purple | 10 | 332 | 97.1 |

TABLE 1-continued

| Parent variety pollinated | A number of individuals F1 is near parent variety | A number of individuals F1 is fringed | Fringed ratio (%) |
|---|---|---|---|
| Heatwave blue with eye | 32 | 427 | 93.0 |
| Yellow magic | 11 | 461 | 94.5 |

F2 seeds were obtained from this F1 plant by self-pollination, these seeds were sowed and 408 germinated seedlings were transfer to pot and bloomed. At least one plant showed fringe flowered and female sterile trait. Namely, if the pollen whose parent is fringed flowered and female sterile is crossed with commercial variety, F1 generation which is fringe flowered weakly and whose pistil also has fertility can be obtained, and at least one individual of 408 individuals of F2 showed the fringe flowered and female sterile character as originals by self-pollinating this F1 generation. Namely, fringe flowered and female sterile Madagascar periwinkle could be bred.

(Breeding of Color Variation Variety)

To flowers of the commercial variety 'Peppermint', 'Stardust orchid', 'Pacifica coral', 'bellarno blue', 'Yellow magic', pollens of flowers (Angel chuchu) which is fringed and female sterile are pollinated and F1 seeds were obtained. This F1 seeds were sowed, grown and used for pollination. Namely, F2 seeds were obtained by pollinating to the pistil of these F1 seeds in the combination described in the following table 2. This F2 seeds were sowed, grown and blossomed. As a result, many flower color varieties of Mandagascar periwinkle which has fringed and sterile flowers were obtained. Namely, as shown in following table 3, Mandagascar periwinkle were obtained which has various patterns of flowers such as color varieties of red, pink, purple, cream and the like, and totally colored, colored at the edge, colored at the inside, and yellow, red, green and the like at the center. Moreover, in this case, the ratio of the fringed and sterile to normal flower is about 1 to 3 in the case of self-pollination of F1 individuals and the ratio of fringed and sterile to normal flowers is 1 to 1 in the case of pollination of the pollen of fringed and sterile flower (cultivar 'Angel chuchu') to F1 individuals. The following table 2 shows the flower color and the color pattern of the obtained color variety. FIG. 2 to FIG. 6 show photos of obtained flowers. In addition, pattern 3, 9, 10, 15 and 17 were obtained from F2 seeds by crossing with other varieties than varieties described above.

TABLE 2

Flower color pattern of F2 individuals of commercial cultivar, pollinated with fringe pollen

| | pattern | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| 5× fringe | | | | 226 | | 6 | | | | | | 3 | | 1 | | | | 218 |
| 12 × 12 | | | | 3 | | 7 | | 3 | | | 15 | | | | | | | 1 |
| 13 × 13 | | 16 | | | | 2 | | | | | | 3 | 3 | 110 | | | | 35 |
| 22 × 22 | 14 | | | 46 | | 14 | | | | | | 44 | | | | | | 8 |
| 2324 × 2324 | | | | 7 | | | | | | | | | | 71 | | 6 | | 3 |

5: Peppermint
12: Stardust Orchid
13: Pacifica Corel
22: bellarno blue (Sakata)
2324: Yellow Magic (The cultivar name after number shows the variety pollinated with the pollen of fringed flower (variety' Angel chuchu), and the number of the left hand column on the table 2 means the number of F1 individual pollinated with pollens of the fringed flowers (cultivar 'Angel chuchu) to the above cultivar. The pattern number of the top column on the table 2 shows the pattern of flower color. Refer to the table 3 for the pattern of the flower color.)

TABLE 3

| number | Color tone | Hem (edge) of petal | Center color |
|---|---|---|---|
| 1 | 1301 buff pink | 1601 pink white | 2504 pale yellow |
| 2 | 9505 bright purple pink | 9502 iris pink | 2504 pale yellow |

TABLE 3-continued

| number | Color tone | Hem (edge) of petal | Center color |
|---|---|---|---|
| 3 | 9506 light purple red | 9501 iris pink | 9506 light purple red |
| 4 | 9501 iris pink | White | 9706 light purple red |
| 5 | 9203 purple pink | 9207 light purple red | 2504 pale yellow |
| 6 | 9203 purple pink | 9707 bright purplish red | 2504 pale yellow |
| 7 | 8604 light purple | | 2504 pale yellow |
| 8 | 8601 purple white | 8604 light purple | 2504 pale yellow |
| 9 | 9702 iris pink | 9707 bright purplish red | 2504 pale yellow |
| 10 | 9701 pink white | 9706 light purplish red | 2504 pale yellow |
| 11 | 1601 pink white | 9204 bright purple red | 2504 pale yellow |
| 12 | 9502 iris pink | 9504 bright purple red | 2504 pale yellow |
| 13 | 9707 clear purplish red | 9707 bright purplish red | 9707 bright purplish red |
| 14 | 9506 bright purplish red | 9506 light purplish red | 9506 light purplish red |
| 15 | 9207 clear purplish red | 9207 bright purplish red | 9207 bright purplish red |
| 16 | 3102 pale greenish yellow | 3102 light greenish yellow | 2504 pale yellow |
| 17 | Green | Total green | green |
| 18 | 0402 pale pink | 0101 pink white | 2504 pale yellow |

In the table the number in front of color shows color chart number by Standard Color Chart of Japan Garden Plant. (Agriculture, Forestry and Fisheries Ministry edited, Plant standard color chart compilation committee compilation, Foundation Japanese color laboratory issued)

The experiment on the flower keeping was performed by using Mandagascar periwinkle comprising fringed and sterile flowers (variety 'Angel chuchu') and 'Pacifica Pink', Mandagascar periwinkle variety with normal fertility. In the inventor's outdoor field, Madagascar periwinkle was grown and observed how many days the bloomed flower continues to bloom. On the bloomed day, tape on which bloomed date was written was twisted around the branch with flower and the day of flower withering was recorded by everyday observation. Each 20 pots were tested under the condition where insects and wind can enter, opening window fully in the greenhouse, and counted from the bloomed date to the date to drop the flower on Pacifica and to the date to wither on the fringe (because the fringed flower does not falls).

The experiment was performed from Mar. 28, 2005 to April 13, watching 20 flowers per every variety. The results are sown in table 4. As shown in the table, about Madagascar periwinkle with fertility, there appeared one whose flower withered on the about forth day after blooming, and after that withered all flowers till the twelfth day in peaking on the seventh day. However, fringed and sterile Madagascar periwinkle was found that the day to wither was dispersed around the twelfth day in peak and that it kept flowers better than fertile Madagascar periwinkle. It is considered that the day to wither is dispersed for nine days on fertile Madagascar periwinkle, because the pollination by wind or by insects varies. On the other hand, sterile and fringe flowered Madagascar periwinkle shows relatively massed distribution focusing on the twelfth day and such distributions are considered due to individual difference.

TABLE 4

The results of Shelf life test of flower

| | Day number after blooming | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| Pacifica pink | | | 1 | 3 | 2 | 6 | 4 | 1 | 2 | 0 | 1 | | | | | | | |
| Fringe | | | | | | | | | | 4 | 3 | 6 | 2 | 1 | 3 | 1 | | |

The number of lower 2 columns in the table shows the number of flowers to wither on the corresponding day.

FIG. 2~6 show the pictures of flowers of fringe flowered Madagascar periwinkles and its explanation is supplemented here. While flowers of the fringe flowered Madagascar periwinkles of FIG. 2~4 bloom overlapping to the extent not to be transparent between five petals, the flowers of the fringe blooming Madagascar periwinkles of FIG. 5 and FIG. 6 form of screw like shape because each petal twists.

Figure 3:
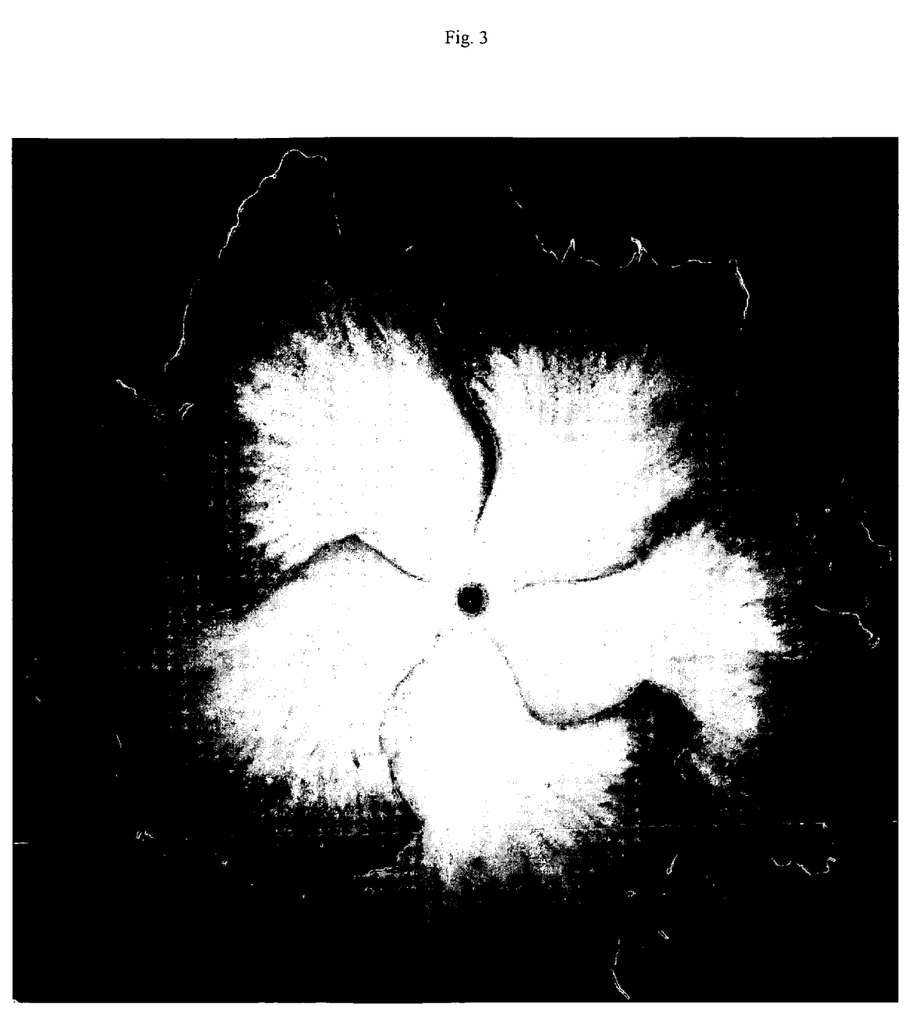

The flower of fringe flowered Madagascar periwinkles shown in FIG. 3 has the high ornamental value, existing coloring at the length 2~5 m at the edge of the petals.

Figure 7:
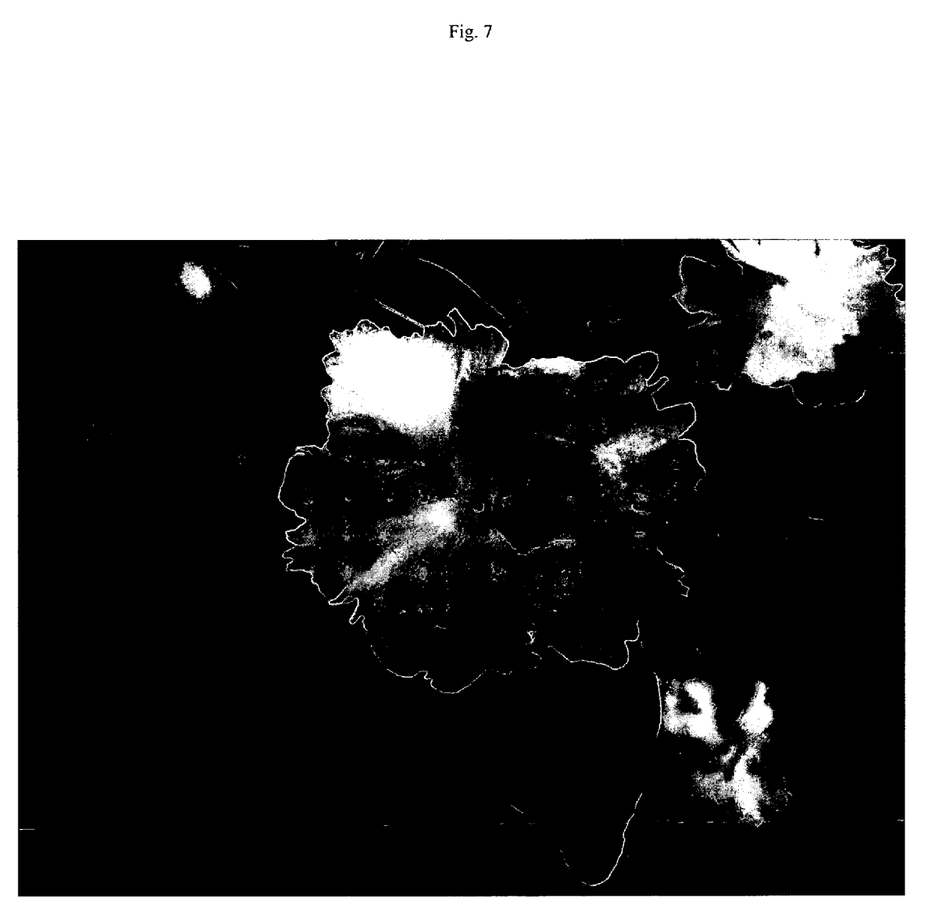
FIG. 7 picture 6 of fringe flowered Madagascar periwinkle

FIG. 7 shows the complete picture of the fringe flowered Madagascar periwinkle which has many flowers in one pot without scent.

From FIG. 2~7 it will be understood that the flower of fringe flowered Madagascar periwinkle on the present invention has notched shape, unlike the shape of round petal as the existing Madagascar periwinkle.

Figure 8:
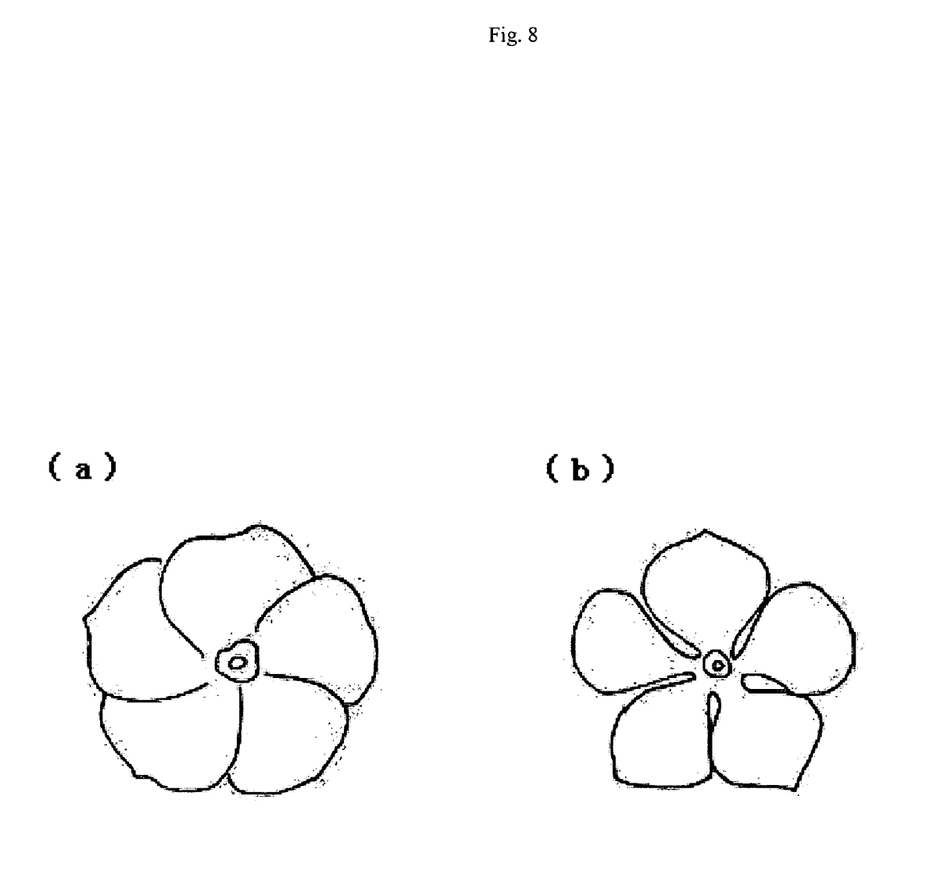
FIG. 8 the kind of the flower shape of Madagascar periwinkle of the existing variety FIG. 9 the shape of tip of petal of Madagascar periwinkle of the existing variety FIG. 10 the flower shape and the shape of tip of petal of Madagascar periwinkle of the present invention
Figure 9:
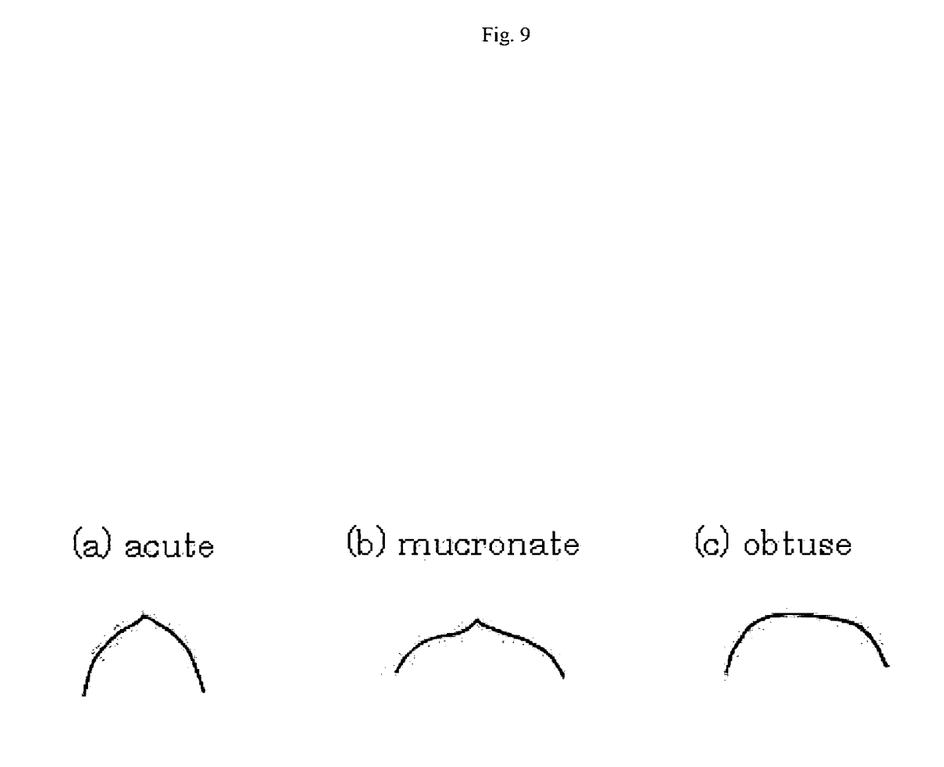

FIG. 8 and FIG. 9 show the kind of the flower shape and the shape of the tip of petals of existing periwinkle (periwinkle of the existing variety). The kind of the flower shapes of existing Madagascar periwinkles is divided to two kinds of (a) without space or (b) with space of FIG. 8 according to with or without space of the round petals between petals. Moreover the shape of tip of petals of existing Madagascar periwinkle is divided into three kinds of (a) acute, (b) mucronate and (c) obtuse.

Figure 10:
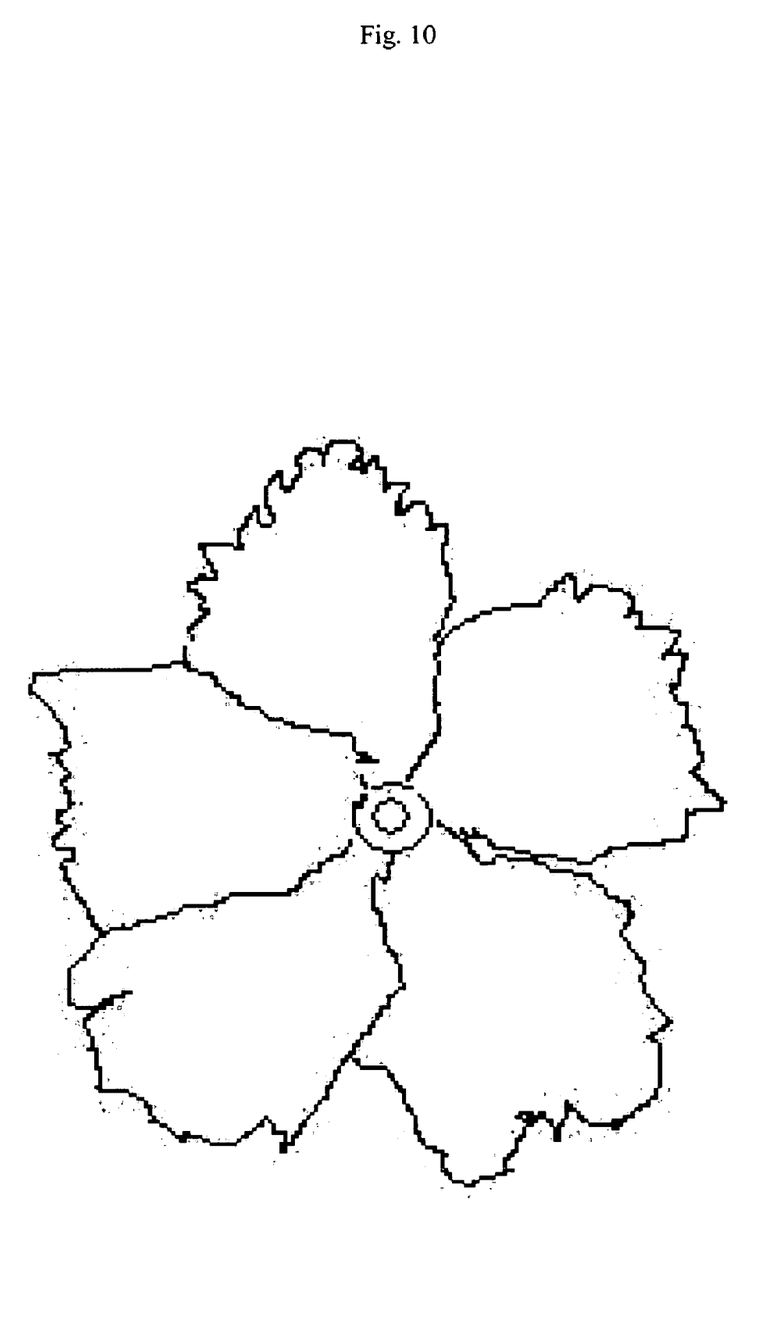

FIG. 10 shows the pattern diagrams of the flower shape and of the shape of the tip of the petals of fringe flowered Madagascar periwinkle on the present invention, and it will be understood that it is different shape of flowers and the shape of the tip of petals from existing Madagascar periwinkle.

Here is the novelty of fringe flowered Madagascar periwinkle relating to the present invention.

What is claimed is:

1. A Madagascar periwinkle variety comprising fringe blooming flowers, a pistil without fertility, a pollen with fertility, and a desired flower color or desired flower shape; said variety obtained by:
   1) crossing an Angel chu-chu line of Madagascar periwinkle with a second Madagascar periwinkle having a desired flower color or desired flower shape to obtain an F1 generation, self-pollinating the F1 generation to obtain F2 progeny, and selecting an F2 individual with fringe blooming flowers, a pistil without fertility, a pollen with fertility, and the desired flower color or the desired flower shape; or said variety obtained by
   2) vegetatively propagating individuals of the variety, obtained by 1) wherein said vegetatively propagated individuals comprise fringe blooming flowers, a pistil without fertility, a pollen with fertility, and the desired flower color or the desired flower shape;
   representative seed of said variety having been deposited under Deposit Number FERM BP-11483.

2. A Madagascar periwinkle variety comprising fringe blooming flowers, a pistil without fertility, a pollen with fertility, marcescent flowers that do not fall when withered, and a desired flower color or desired flower shape; said variety obtained by:
   1) crossing an Angel chu-chu line of Madagascar periwinkle with a second Madagascar periwinkle having a desired flower color or desired flower shape to obtain an F1 generation, self-pollinating the F1 generation to obtain F2 progeny, and selecting an F2 individual with fringe blooming flowers, a pistil without fertility, a pollen with fertility, marcescent flowers that do not fall when withered, and the desired flower color or the desired flower shape; or said variety obtained by
   2) vegetatively propagating individuals of the variety, obtained by 1) wherein said vegetatively propagated individuals comprise fringe blooming flowers, a pistil without fertility, a pollen with fertility, marcescent flowers that do not fall when withered, and the desired flower color or the desired flower shape;
   representative seed of said variety having been deposited under Deposit Number FERM BP-11483.

3. A cell, an organ, a tissue, a plant body, or a seed of the Madagascar periwinkle variety according to any one of claims 1 and 2.

Figure 2:
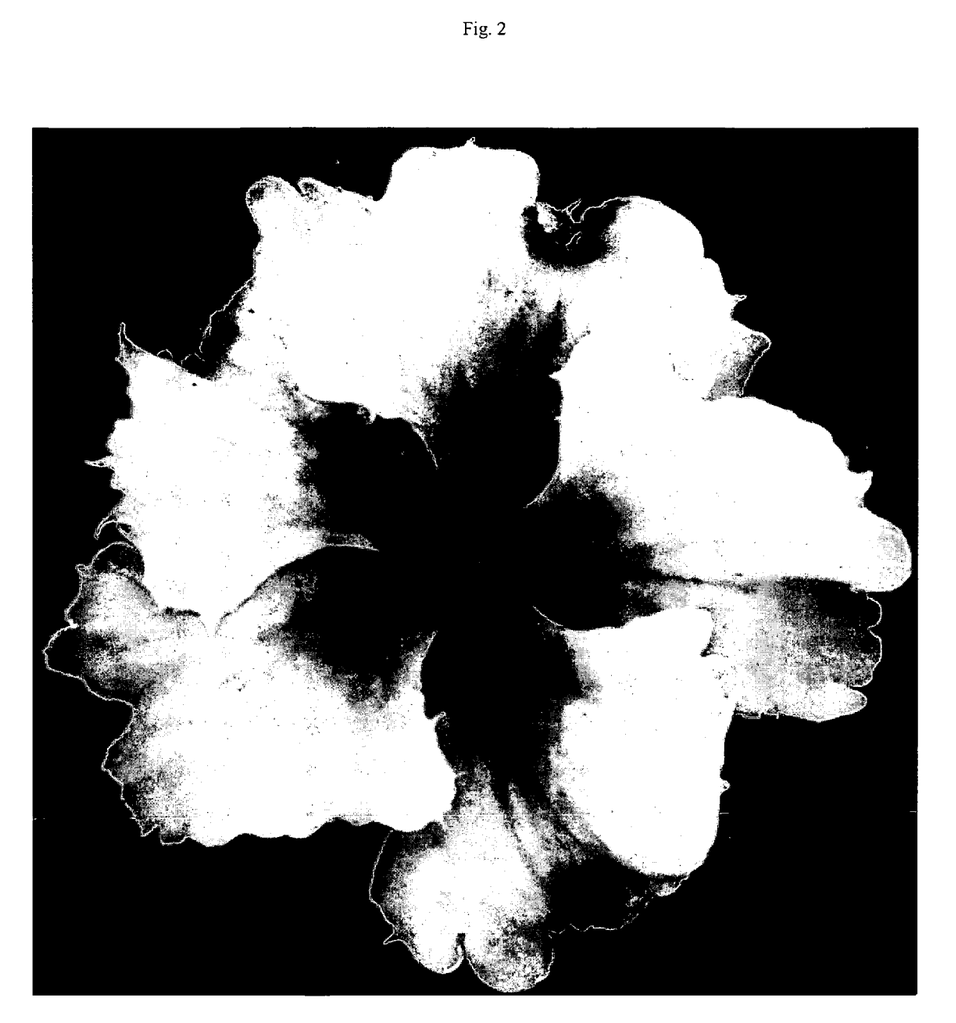
FIG. 2 flower's picture 1 of color changed variety of fringe flowered Madagascar periwinkle FIG. 3 flower's picture 2 of color changed variety of fringe flowered Madagascar periwinkle FIG. 4 flower's picture 3 of color changed variety of fringe flowered Madagascar periwinkle FIG. 5 flower's picture 4 of fringe flowered Madagascar periwinkle (the flower shape is screwed)
Figure 4:
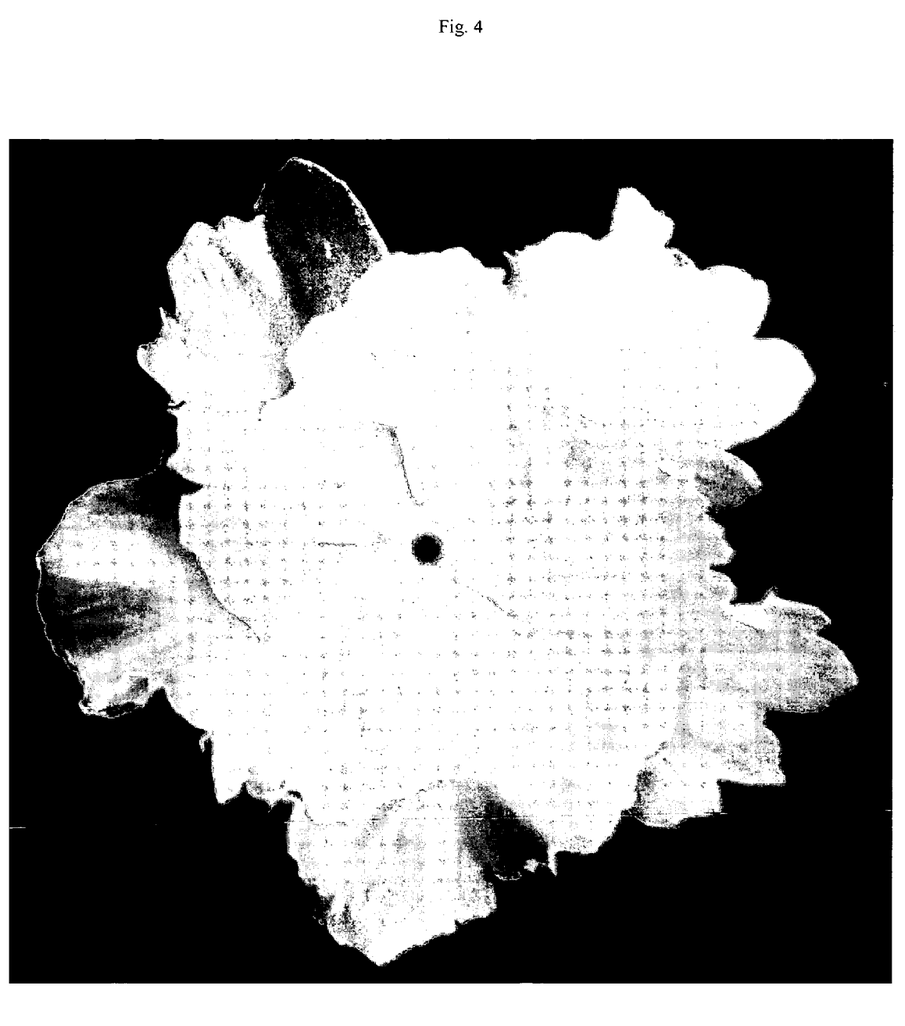

4. The Madagascar periwinkle variety according to claim 1 and having fringe flowers with various color patterns selected from the group consisting of totally colored, colored at the edge, and colored at the inside as depicted in FIGS. 2, 3 and 4.

Figure 5:
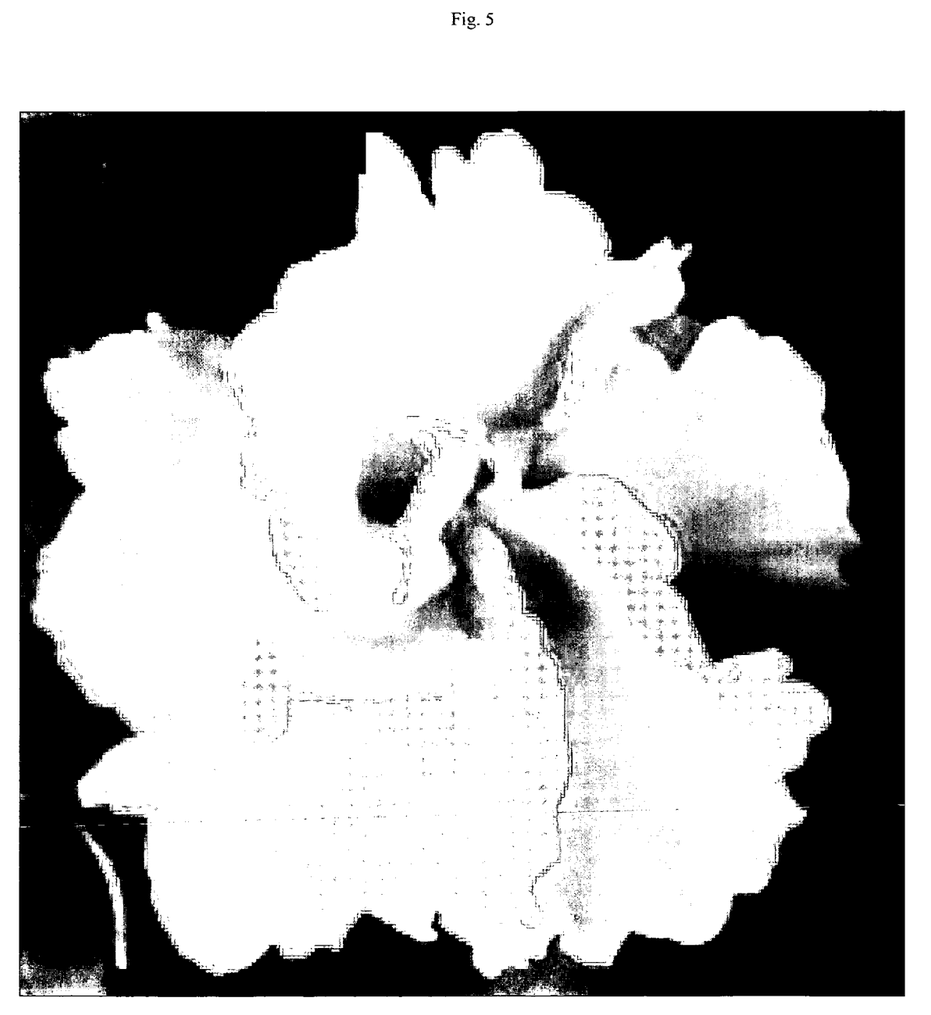

5. The Madagascar periwinkle variety according to claim 1 and having fringe flowers with a shape as depicted in FIG. 5.

Figure 6:
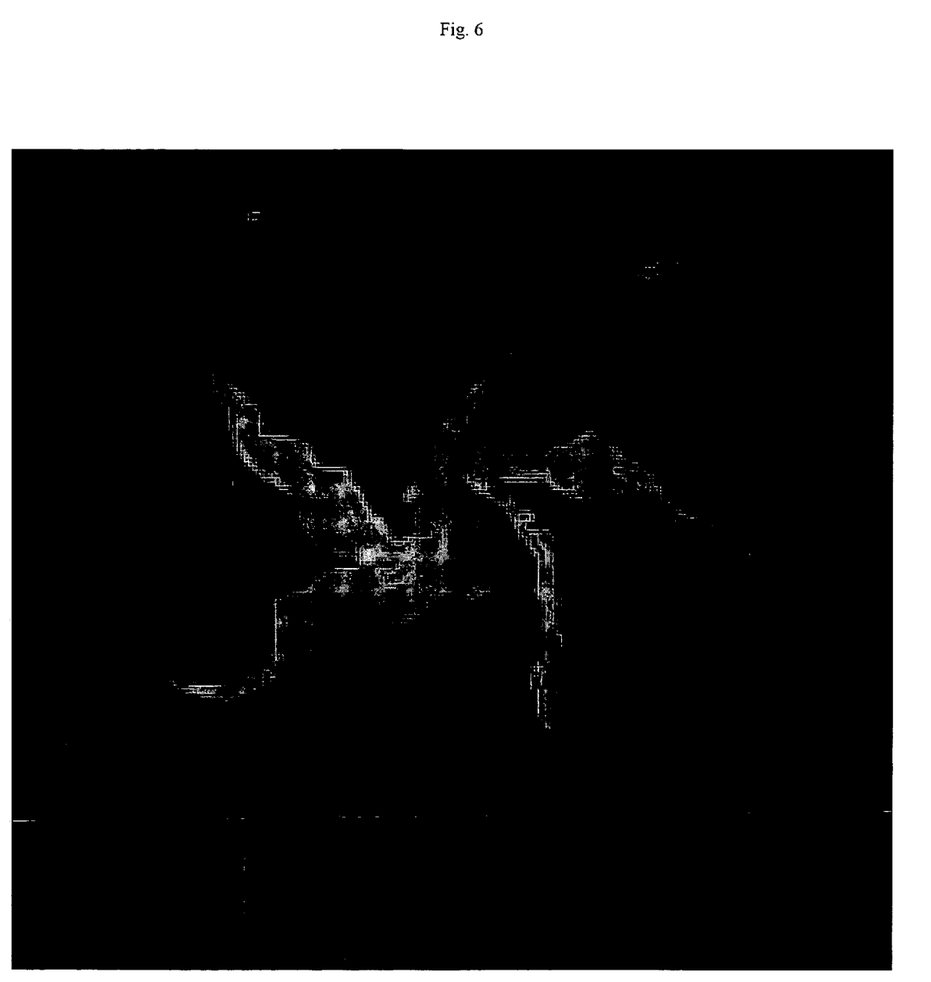
FIG. 6 flower's picture 5 of fringe flowered Madagascar periwinkle (the flower shape is screwed)

6. The Madagascar periwinkle variety according to claim 1 and having fringe flowers with a shape as depicted in FIG. 6.

7. The Madagascar periwinkle variety according to claim 1 and having fringe flowers with a shape as depicted in FIG. 7.

8. The Madagascar periwinkle variety according to claim 2 and having fringe flowers with various color patterns selected from the group consisting of totally colored, colored at the edge, and colored at the inside as depicted in FIGS. 2, 3 and 4.

9. The Madagascar periwinkle variety according to claim 2 and having fringe flowers with a shape as depicted in FIG. 5.

10. The Madagascar periwinkle variety according to claim 2 and having fringe flowers with a shape as depicted in FIG. 6.

11. The Madagascar periwinkle variety according to claim 2 and having fringe flowers with a shape as depicted in FIG. 7.

* * * * *